United States Patent
Ko et al.

(10) Patent No.: US 9,402,577 B2
(45) Date of Patent: Aug. 2, 2016

(54) DRIVER'S FATIGUE DETECTION SYSTEM AND METHOD

(71) Applicant: AUTOMOTIVE RESEARCH & TEST CENTER, Changhua County (TW)

(72) Inventors: Ming-Kuan Ko, Changhua County (TW); Yen-Cheng Feng, Changhua County (TW)

(73) Assignee: Automotive Research & Test Center, Changhua County (TW)

( * ) Notice: Subject to any disclaimer, the term of this patent is extended or adjusted under 35 U.S.C. 154(b) by 121 days.

(21) Appl. No.: 14/580,629

(22) Filed: Dec. 23, 2014

(65) Prior Publication Data

US 2016/0174890 A1    Jun. 23, 2016

(51) Int. Cl.
| | |
|---|---|
| G08B 23/00 | (2006.01) |
| A61B 5/18 | (2006.01) |
| A61B 5/00 | (2006.01) |
| B60W 40/08 | (2012.01) |

(52) U.S. Cl.
CPC .............. *A61B 5/18* (2013.01); *A61B 5/0077* (2013.01); *A61B 5/6893* (2013.01); *A61B 5/742* (2013.01); *A61B 5/7405* (2013.01); *A61B 5/746* (2013.01); *B60W 40/08* (2013.01); *B60W 2040/0827* (2013.01)

(58) Field of Classification Search
CPC .......... G08B 23/00; G08B 21/00; A61B 5/18
USPC ................. 340/576, 573.1, 575; 180/272
See application file for complete search history.

(56) References Cited

U.S. PATENT DOCUMENTS

| | | | | |
|---|---|---|---|---|
| 6,946,966 | B2 | 9/2005 | Koenig | |
| 7,138,923 | B2* | 11/2006 | Ferrone | G08B 21/06 180/272 |
| 8,396,630 | B2* | 3/2013 | Barnett | B62D 7/20 180/204 |
| 8,519,853 | B2* | 8/2013 | Eskandarian | A61B 5/6887 180/272 |
| 8,725,311 | B1* | 5/2014 | Breed | G08B 21/06 600/300 |
| 2011/0105925 | A1* | 5/2011 | Hatakeyama | A61B 5/0245 600/509 |

FOREIGN PATENT DOCUMENTS

| | | |
|---|---|---|
| CN | 202313288 U | 7/2012 |
| CN | 292313277 Y | 7/2012 |
| TW | M442958 | 12/2012 |

* cited by examiner

*Primary Examiner* — Toan N Pham
(74) *Attorney, Agent, or Firm* — Rosenberg, Klein & Lee

(57) ABSTRACT

The present invention discloses a driver's fatigue detection system and method. The system comprises a vital sign detection device generating at least one personal vital sign value; a storage device storing a linear statistic equation; a processor electrically connected with the vital sign detection device and the storage device; and a display device electrically connected with the processor. The processor receives the personal vital sign value, retrieves the linear statistic equation, substitutes the personal vital sign value into the linear statistic equation to generate a predictive vehicle deviation value, and determines whether the predictive vehicle deviation value is over a preset vehicle deviation value. If yes, the processor generates an alert signal to the display device to present an alert image. The present invention determines whether the stability of the driver is decreasing according to his physiological status and reminds the driver to avoid a traffic accident beforehand.

13 Claims, 4 Drawing Sheets

DRIVER'S FATIGUE DETECTION SYSTEM AND METHOD

BACKGROUND OF THE INVENTION

1. Field of the Invention

The present invention relates to a technology for monitor a driver, particularly to a driver's fatigue detection system and method.

2. Description of the Related Art

Most traffic accidents are attributed to personal factors of drivers, such as attention deficit, fatigue or diseases. Therefore, many driving safety systems respond to the abnormal driver himself or the abnormal driving behavior, including LDWS (Lane Departure Warning System), FCW (Forward Collision Warning), and AES (Autonomous Emergency System).

However, only few systems are addressed to monitor the physiological status of a driver. Each one has his own personal fatigue withstanding ability. if the physiological status is determined according to a single standard, the driving safety system may over-respond or under-respond, which may trouble or endanger the driver.

Accordingly, the present invention proposes a driver's fatigue detection system and method to solve the abovementioned problems.

SUMMARY OF THE INVENTION

The primary objective of the present invention is to provide a driver's fatigue detection system and method, which persistently collect the information of physiological statuses and the vehicle deviations of a driver to statistically work out a linear equation, and alerts the driver of the possibility of a vehicle deviation according to the output value of the linear equation before the vehicle deviation takes place actually, whereby the present invention can prevent the driver from further weakening in the physiological status and exempt the driver from a traffic accident.

Another objective of the present invention is to provide a driver's fatigue detection system and method, which uses a plurality of sensors to detect the status of a driver from different aspects, whereby to detect the physiological status of the driver more accurately.

To achieve the abovementioned objectives, the present invention proposes a driver's fatigue detection method, which comprises steps: a processor acquiring a plurality of reference vital sign values and a plurality of reference vehicle deviation values from a detection device; the processor statistically process the reference vital sign values and the reference vehicle deviation values to generate a linear statistic equation; the processor receiving a personal vital sign value from the detection device, and substituting the personal vital sign values into the linear statistic equation to generate a predictive vehicle deviation value; the processor determining whether the predictive vehicle deviation value is over a preset vehicle deviation value; if the predictive vehicle deviation value is over a preset vehicle deviation value, the processor generating an alert signal; if the predictive vehicle deviation value is not over a preset vehicle deviation value, the process returning to the step of receiving a personal vital sign value.

The present invention also proposes a driver's fatigue detection system, which comprises a vital sign detection device, a storage device, a processor electrically connected with the vital sign detection device and the storage device, and a display device electrically connected with said processor. The vital sign detection device generates at least one personal vital sign value to the processor. The storage device stores a linear equation. The processor receives the personal vital sign value from the vital sign detection device, downloads the linear equation from the storage device, and substitutes the personal vital sign value into the linear equation to generate a predictive vehicle deviation value. The processor further determines whether the predictive vehicle deviation value is over a preset vehicle deviation value. If the predictive vehicle deviation value is over a preset vehicle deviation value, the processor generates an alert signal to the display device, and the display device presents an alert image according to the alert signal.

Below, embodiments are described in detail to make easily understood the objectives, technical contents, characteristics and accomplishments of the present invention.

DETAILED DESCRIPTION OF THE INVENTION

Figure 1:
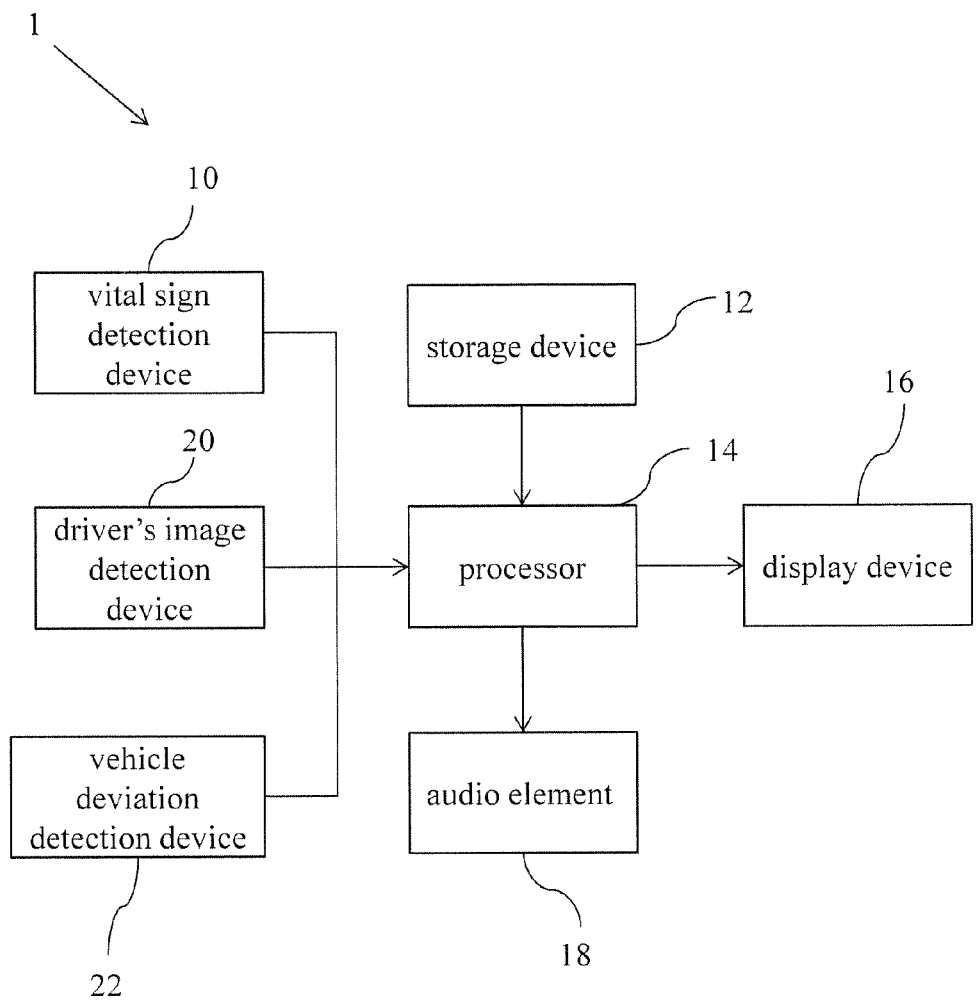
FIG. 1 is a block diagram schematically showing a driver's fatigue detection system according to embodiments of the present invention.

Refer to FIG. 1 a block diagram schematically showing a driver's fatigue detection system according to embodiments of the present invention. The driver's fatigue detection system 1 of the present invention comprises a vital sign detection device 10 generating a personal vital sign value; a storage device 12 storing a linear statistic equation; a processor 14 electrically connected with the vital sign detection device 10 and the storage device 12; and a display device 16 electrically connected with the processor 14. The processor 14 receives the personal vital sign value from the vital sign detection device 10 and downloads the linear statistic equation from the storage device 12. The processor 14 substitutes the personal vital sign value into the linear statistic equation to generate a predictive vehicle deviation value. Next, the processor 14 determines whether the predictive vehicle deviation value is over a preset vehicle deviation value. If the predictive vehicle deviation value is over a preset vehicle deviation value, the processor 14 generates an alert signal to the display device 16. According to the alert signal, the display device 16 presents an alert image to alert the driver. In one embodiment, an audio element 18 is electrically connected with the processor 14, receiving the alert signal and generating an alert sound according to the alert signal to alert the driver and remind the driver that his physiological status is weak. In addition to detecting fatigue, the vital sign detection device 10 also detects alcohol concentration, diseases, or other symptoms in some embodiments. The linear statistic equation (1) states the relationship between the predictive vehicle deviation value and the personal vital sign value and is expressed as $$X=\beta Y+C \quad (1)$$

wherein X is the predictive vehicle deviation value, Y the personal vital sign value, C a constant, and β the slope.

Refer to FIG. 1 again. In one embodiment, the linear statistic equation states the relationship of the predictive vehicle deviation value, the personal vital sign value and the personal driver's image value and is expressed as $$X = \beta Y + C_Z + C \quad (2)$$

wherein X is the predictive vehicle deviation value, Y the personal vital sign value, Cz the personal driver's image value, C a constant, and β the slope. In addition to the vital sign detection device 10 and the storage device 12, the processor 14 is further electrically connected with a driver's image detection device 20 in this embodiment. The driver's image detection device 20 captures the images of eye opening and eye closing of the driver and the images of the head swings of the driver, determines whether the driver is fatigued according to the images, and generates a personal driver's image value to the processor 14. The processor 14 substitutes the personal driver's image value into the linear statistic equation (2) to generate a predictive vehicle deviation value. Substituting the personal driver's image value into the equation is to increase the accuracy of calculation. The user can decide whether to substitute the personal driver's image value into the equation according to his own requirement while calculating the predictive vehicle deviation value.

Thus, while only receiving the personal vital sign value, the processor 14 uses the linear statistic equation (1) to generate the predictive vehicle deviation value. While receiving the personal vital sign value and the personal driver's image value, the processor 14 uses the linear statistic equation (2) to generate the predictive vehicle value.

Figure 2:
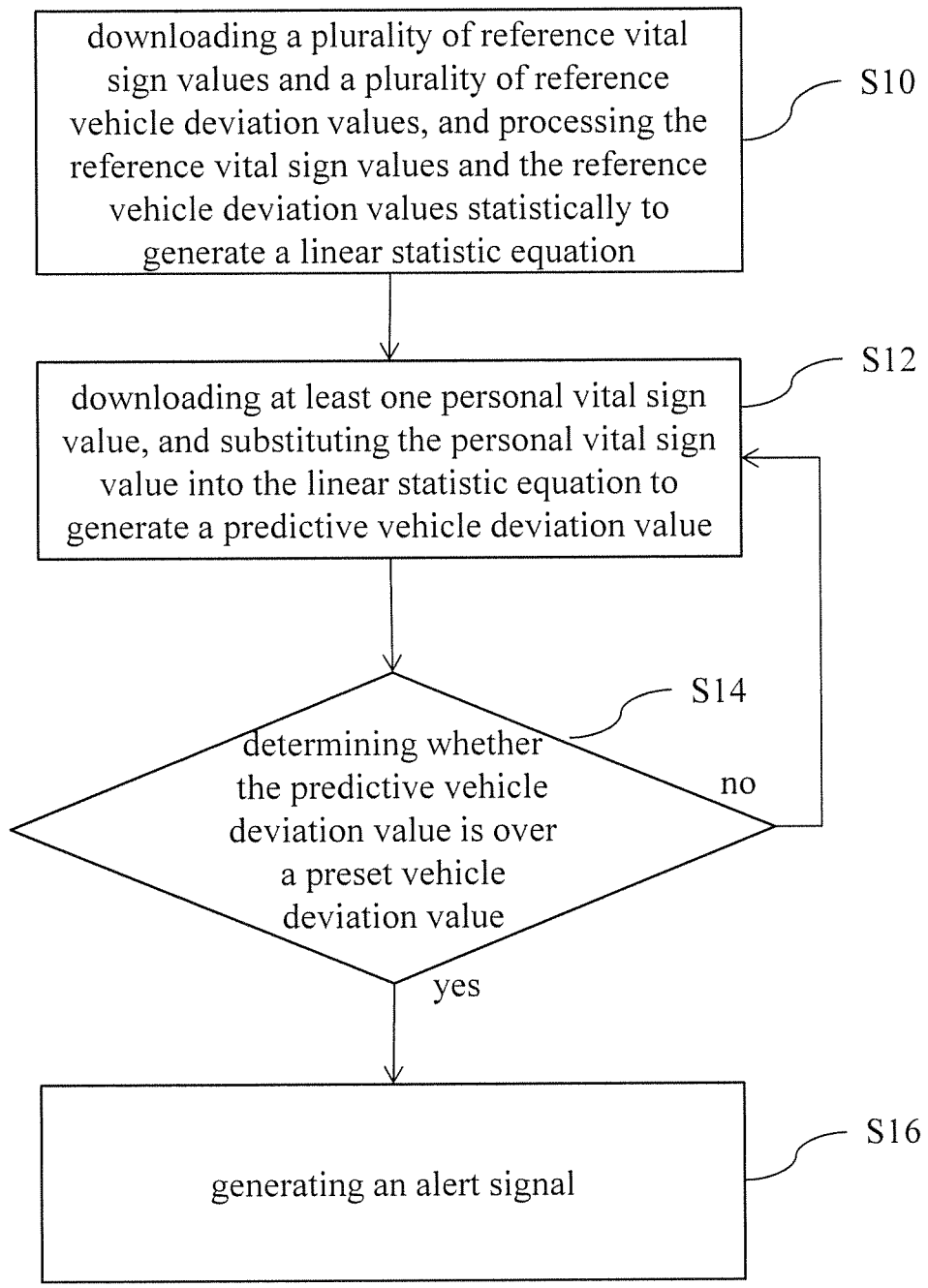
FIG. 2 is a flowchart of a driver's fatigue detection method according to one embodiment of the present invention.
Figure 3:
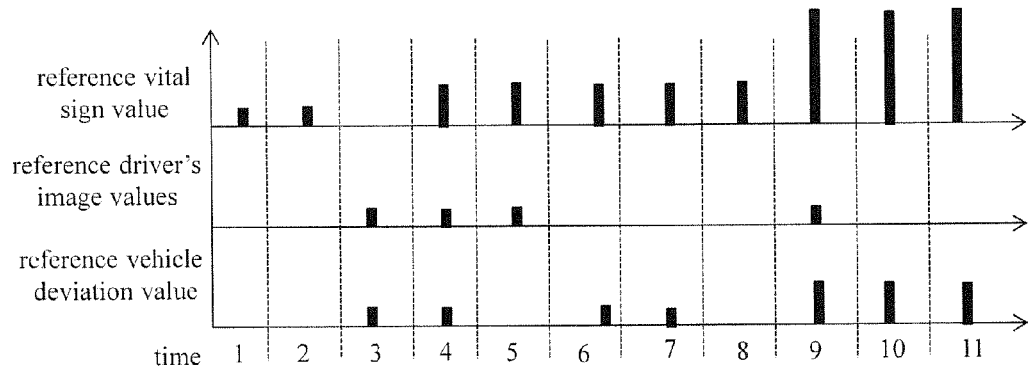
FIG. 3 is a table recording the values downloaded at different time points according to one embodiment of the present invention.
Figure 4:
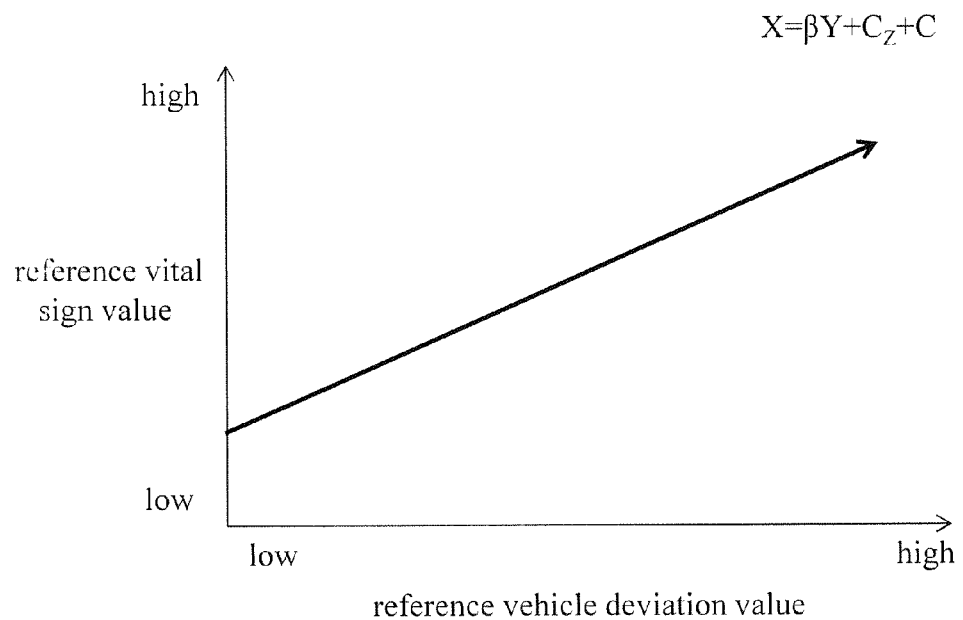
FIG. 4 is a diagram schematically showing a linear statistic equation according to one embodiment of the present invention.

The architecture of the driver's fatigue detection system has been described hereinbefore. The process of the driver's fatigue detection method of the present invention and the generation of the linear statistic equation will be described thereinafter. Refer to FIG. 1 and FIG. 2. In step S10, a vital sign detection device 10 generates a plurality of reference vital sign values, and a vehicle deviation detection device 22 generates a plurality of reference vehicle deviation values. A processor 14 downloads the reference vital sign values and the reference vehicle deviation values. In some embodiments, the processor 14 also downloads reference driver's image values generated by a driver's image detection device 20 at the same time. Thus, the processor 14 generates the table shown in FIG. 3. The table uses bars to represent the reference vital sign values, the reference vehicle deviation values and the reference driver's image values downloaded at different time points. The longer the bar, the higher the value. At the third time point, the reference driver's image value rises. It indicates the driver is splitting his attention from driving. At the same time point, the reference vehicle deviation value indicates that the vehicle is deviating from the lane. Thus, the vehicle deviation at the third time point is not due to the physiological status of the driver but attributed to the attention deficit of the driver. Therefore, the reference vehicle deviation value and the reference driver's image value at the third time point are filtered out lest they interfere with the statistics. Refer to FIG. 4. After receiving the reference vital sign values and the reference vehicle deviation values, the processor 14 plots a straight line according to the reference values and generates a linear statistic equation (1) expressed as $$X = \beta Y + C \quad (1)$$

wherein X is the predictive vehicle deviation value, Y the personal vital sign value, C a constant, and β the slope.

In one embodiment, the personal driver's image value is added to the linear statistic equation to form a linear statistic equation (2) expressed as $$X = \beta Y + C_Z + C \quad (2)$$

wherein X is the predictive vehicle deviation value, Y the personal vital sign value, Cz the personal driver's image value, C a constant, and β the slope. The linear statistic equation (2) is different from the linear statistic equation (1) only in that the personal driver's image value is added to the linear statistic equation (2). The addition of the personal driver's image value is to increase the accuracy of the predictive vehicle deviation value. The linear statistic equation is stored in a storage device 12 as a personal linear statistic equation.

Whether the linear statistic equation (1) or the linear statistic equation (2) is to be used to generate the predictive vehicle deviation value is dependent on whether the processor 14 receives only the personal vital sign value or both the personal vital sign value and the personal driver's image value. While only receiving the personal vital sign value, the processor 14 uses the linear statistic equation (1) to generate the predictive vehicle deviation value. While receiving both the personal vital sign value and the personal driver's image value, the processor 14 uses the linear statistic equation (2) to generate the predictive vehicle value so as to increase the accuracy of the predictive vehicle deviation value.

Refer to FIG. 1 and FIG. 2 again. In the embodiment, the linear statistic equation (2) is used. After the linear statistic equation (2) is generated and stored in the storage device 12 in Step S10, the process proceeds to Step S12. In Step S12, the user is verified by an authentication process and allowed to retrieve his personal linear statistic equation (2); the vital sign detection device 10 acquires a personal vital sign value, and the driver's image detection device 20 acquires a personal driver's image value; the processor 14 substitutes the personal vital sign value and the personal driver's image value into the linear statistic equation (2) to generate a predictive vehicle deviation value. Substituting the personal driver's image value is optional. However, substitution of the personal driver's image value can increase the accuracy of the predictive vehicle deviation value. Thus, this embodiment adopts the linear statistic equation (2), and the personal driver's image value is substituted into the linear statistic equation (2).

After the predictive vehicle deviation value is generated, the process proceeds to Step S14. In Step S14, the processor 14 determines whether the predictive vehicle deviation value is over a preset vehicle deviation value. If the predictive vehicle deviation value is over the preset vehicle deviation value, the process proceeds to Step S16. In Step S16, the processor 14 generates an alert signal to a display device 16 and an audio element 18. On receiving the alert signal, the display device 16 and the audio element 18 respectively generate an alert image and an alert sound to remind the driver that his physiological status may cause the vehicle to deviate from the lane. If the predictive vehicle deviation value is not over the preset vehicle deviation value, the process returns to Step S12 where the processor 14 continues to respectively download the personal vital sign value and the personal driver's image value from the vital sign detection device 10 and the driver's image detection device 20 and continues to determine whether the driver is suitable to keep on driving the vehicle. Besides, the processor 14 also persistently receives the personal vehicle deviation values generated by a vehicle deviation detection device 22. According to the personal vehicle deviation values and personal vital sign values, the processor 14 persistently modifies the linear statistic equation to generate a linear statistic equation further more adaptive to an individual. In some embodiments, the alert signals are classified into a low-level alert signal, a medium-level alert signal and a high-level alert signal according to a low-level vehicle-deviation alert value and a medium-level vehicle-deviation alert value in the processor 14. If the predictive vehicle deviation value is below the low-level vehicle-deviation alert value, the processor 14 generates a low-level alert signal to the display device 16 and the audio element 18 to enable the display device 16 and the audio element 18 to respectively generate a low-level alert image and a low-level alert sound. If the predictive vehicle deviation value is between the low-level vehicle-deviation alert value and the medium-level vehicle-deviation alert value, the processor 14 generates a medium-level alert signal to the display device 16 and the audio element 18 to enable the display device 16 and the audio element 18 to respectively generate a medium-level alert image and a medium-level alert sound. If the predictive vehicle deviation value is over the medium-level vehicle-deviation alert value, the processor 14 generates a high-level alert signal to the display device 16 and the audio element 18 to enable the display device 16 and the audio element 18 to respectively generate a high-level alert image and a high-level alert sound. Different levels of alert signals are to remind the driver to take different actions. The medium-level alert signal reminds the driver that his physiological status has reached a critical point to cause a vehicle deviation and that if his physiological status keeps weakening, the vehicle would deviate from the lane actually. Therefore, on receiving the medium-level alert signal, the driver should try to recover his physical strength. The high-level alert signal reminds the driver that the vehicle has deviated from the lane severely and that his physiological status is pretty abnormal. On receiving the high-level alert signal, the driver should park and take a rest lest a traffic accident occur.

In conclusion, the present invention persistently collects the information of the vital sign values and vehicle deviation values of an identical driver to statistically work out a linear equation. According to the output of the linear equation, the present invention reminds the driver that his current physiological status may cause the vehicle to deviate from the lane before the vehicle actually deviates. Owing to the reminder, the driver will park for taking a rest to recover his physical strength lest a traffic accident occur. Besides, the present invention uses a plurality of sensors to detect the physiological status of a driver from different aspects and thus can more effectively monitor the personal physiological status of the driver.

The embodiments described above are only to exemplify the present invention but not to limit the scope of the present invention. Any equivalent modification or variation according to the characteristic or spirit of the present invention is to be also included within the scope of the present invention.

What is claimed is:

1. A driver's fatigue detection method, comprising
   Step (A): a detection device inputting a plurality of reference vital sign values and a plurality of reference vehicle deviation values to a processor, and said processor processing said reference vital sign values and said reference vehicle deviation values statistically to generate a linear statistic equation;
   Step (B): said detection device inputting at least one personal vital sign value to said processor, and said processor substituting said personal vital sign value into said linear statistic equation to generate a predictive vehicle deviation value; and
   Step (C): said processor determining whether said predictive vehicle deviation value is over a preset vehicle deviation value; if yes, said processor generating an alert signal; if no, returning to said Step (B).

2. The driver's fatigue detection method according to claim 1, wherein in said Step (A), a plurality of reference driver's image values is also input to said processor in addition to said reference vital sign values and said reference vehicle deviation values, and wherein if one said reference driver's image value indicates a driver is splitting his attention and if one said reference vehicle deviation value detected at an identical time point indicates that a vehicle driven by said driver is deviating from a lane, said reference driver's image value and said reference vehicle deviation value are filtered out.

3. The driver's fatigue detection method according to claim 1, wherein in said Step (B), a personal driver's image value is also input to said processor in addition said personal vital sign value; said processor also substitutes said personal driver's image value into said linear statistic equation to generate said predictive vehicle deviation value.

4. The driver's fatigue detection method according to claim 3, wherein in said linear statistic equation, said predictive vehicle deviation value equals to said personal vital sign value multiplied by a slope plus said personal driver's image value and plus a constant.

5. The driver's fatigue detection method according to claim 1, wherein in said Step (C), said preset vehicle deviation value is one of a low-level vehicle-deviation alert value and a medium-level vehicle-deviation alert value; if said predictive vehicle deviation value is below said low-level vehicle-deviation alert value, said processor generates a low-level alert signal; if said predictive vehicle deviation value is between said low-level vehicle-deviation alert value and said medium-level vehicle-deviation alert value, said processor generates a medium-level alert signal; if said predictive vehicle deviation value is over said medium-level vehicle-deviation value, said processor generates a high-level alert signal.

6. The driver's fatigue detection method according to claim 1, wherein in said Step (B), said processor receives a personal vehicle deviation value and said personal vital sign value, and uses said personal vehicle deviation value and said personal vital sign value to update said linear statistic equation.

7. A driver's fatigue detection system comprising
   a vital sign detection device generating at least one personal vital sign value;
   a storage device storing a linear statistic equation;
   a processor electrically connected with said vital sign detection device and said storage device, receiving said personal vital sign value, retrieving said linear statistic equation, substituting said personal vital sign value into said linear statistic equation to generate a predictive vehicle deviation value, determining whether said predictive vehicle deviation value is over a preset vehicle deviation value, and generating an alert signal if said predictive vehicle deviation value is over said preset vehicle deviation value; and
   a display device electrically connected with said processor, receiving said alert signal, presenting an alert image according to said alert signal.

8. The driver's fatigue detection system according to claim 7, wherein said display device includes an audio element that is electrically connected with said processor, receives said alert signal, and generates an alert sound according to said alert signal.

9. The driver's fatigue detection system according to claim 7, wherein a driver's image detection device is electrically connected with said processor and generates a personal driver's image values to said processor; said processor also substitutes said personal driver's image value into said linear statistic equation to generate said predictive vehicle deviation value.

10. The driver's fatigue detection system according to claim 9, wherein in said linear statistic equation, said predictive vehicle deviation equals to said personal vital sign value multiplied by a slope plus said personal driver's image value and plus a constant.

11. The driver's fatigue detection system according to claim 7, wherein said preset vehicle deviation value is one of a low-level vehicle-deviation alert value and a medium-level vehicle-deviation alert value; if said predictive vehicle deviation value is below said low-level vehicle-deviation alert value, said processor generates a low-level alert signal to said display device to enable said display device to present a low-level alert image; if said predictive vehicle deviation value is between said low-level vehicle-deviation alert value and said medium-level vehicle-deviation alert value, said processor generates a medium-level alert signal to said display device to enable said display device to present a medium-level alert image; if said predictive vehicle deviation value is over said medium-level vehicle-deviation value, said processor generates a high-level alert signal to said display device to enable said display device to present a high-level alert image.

12. The driver's fatigue detection system according to claim 7 further comprising a vehicle deviation detection device electrically connected with said processor, wherein said vehicle deviation detection device generates a plurality of reference vehicle deviation values, and said vital sign detection device generates a plurality of reference vital sign values, and wherein said processor uses said reference vital sign values and said reference vehicle deviation values to generate said linear statistic equation.

13. The driver's fatigue detection system according to claim 12, wherein said vehicle deviation detection device also generates at least one personal vehicle deviation value to said processor; said processor uses said personal vehicle deviation value and said personal vital sign value to update said linear statistic equation.

* * * * *